United States Patent
Rolf (10) Patent No.: US 6,406,712 B1
(45) Date of Patent: Jun. 18, 2002

(54) AQUEOUS GEL AND PACKAGE FOR A WOUND DRESSING AND METHOD

(75) Inventor: David Rolf, Minneapolis, MN (US)

(73) Assignee: LecTec Corporation, Minnetonka, MN (US)

( * ) Notice: Subject to any disclaimer, the term of this patent is extended or adjusted under 35 U.S.C. 154(b) by 0 days.

(21) Appl. No.: 08/328,619

(22) Filed: Oct. 25, 1994

Related U.S. Application Data (63) Continuation of application No. 07/774,064, filed on Oct. 9, 1991, now abandoned.

(51) Int. Cl.[7] ................................................ A61K 9/70
(52) U.S. Cl. ........................ 424/445; 424/443; 424/447
(58) Field of Search ................................ 424/443, 445, 424/447; 426/108

(56) References Cited

U.S. PATENT DOCUMENTS

| | | |
|---|---|---|
| 2,249,536 A | 7/1941 | McDowell |
| 2,249,537 A | 7/1941 | McDowell |
| 2,249,538 A | 7/1941 | McDowell |
| 2,441,729 A | 5/1948 | Steiner |
| 2,477,861 A | 8/1949 | Clark et al. |
| 2,653,610 A | 9/1953 | Smith |
| 2,653,611 A | 9/1953 | Smith |
| 2,741,559 A | 4/1956 | Banowitz |
| 2,756,874 A | 7/1956 | Erickson |
| 3,008,835 A | 11/1961 | Madding |
| 3,207,420 A | 9/1965 | Navarrette-Kindelán |
| 3,251,781 A | 5/1966 | Jordan |
| 3,265,631 A | 8/1966 | Jordan |
| 3,293,048 A | 12/1966 | Kitterman |
| 3,301,723 A | 1/1967 | Chrisp |
| 3,550,592 A | 12/1970 | Bernardin |

(List continued on next page.)

FOREIGN PATENT DOCUMENTS

| | | |
|---|---|---|
| DE | 3601 132 | 7/1987 |
| EP | 0302536 | 8/1989 |
| EP | 0405993 | 1/1991 |
| GB | 2182663 A | 11/1985 |
| GB | 2194144 A | 3/1988 |
| GB | 2229443 | 9/1990 |
| SE | 7712360-2 | 5/1979 |

OTHER PUBLICATIONS

"Current and future trends in wound management 2: Modern Surgical dressings"; *Pharmacy International*, Jun. 1985, pp. 131–134.

"Wound Dressings"; *Pharmacy Update*, Apr. 1987, pp. 147–150.

Commercial Product: Antibody Product by Land O'Lakes.

*Primary Examiner*—Raj Bawa
(74) *Attorney, Agent, or Firm*—Schwegman, Lundberg, Woessner & Kluth, P.A.

(57) ABSTRACT

A solid elastic and pliable self-supporting wound dressing is formed by mixing dry hydrocolloid polymer powder with water. Preferably the dry polymer powder and water are contained in a sealed package having a temporary or manually-removable barrier so that the dry polymer and waster can be stored separately from each other while in the package. The wound dressing may be prepared by breaking or removing the barrier to allow intermixing of the polymer and water within the package so that a fluid, pourable and spreadable aqueous colloidal dispersion is initially formed within the package and which can be removed from the package and easily poured or spread onto the wound. The initially-formed dispersion then solidifies to form a solid or semi-solid elastic, pliable wound dressing containing water and hydrocolloid. The presence of water in the wound dressing provides desirable moisture during the healing process. Preferably the package is made from flexible plastic with a temporary heat-seal barrier between the dry polymer and water. A gelling or crosslinking agent may be also be used to improve the characteristics of some hydrocolloids.

15 Claims, 2 Drawing Sheets

U.S. PATENT DOCUMENTS

| | | |
|---|---|---|
| 3,637,132 A | 1/1972 | Gray |
| 3,972,328 A | 8/1976 | Chen |
| 4,071,467 A | 1/1978 | Nordgren |
| 4,090,013 A | 5/1978 | Ganslaw et al. |
| 4,333,461 A | 6/1982 | Muller |
| 4,393,048 A | 7/1983 | Mason, Jr. |
| 4,410,321 A | 10/1983 | Pearson et al. |
| 4,550,825 A | 11/1985 | Sutryn et al. |
| 4,563,174 A | 1/1986 | Dupont et al. |
| 4,596,713 A | 6/1986 | Burdette |
| 4,613,497 A | 9/1986 | Chavkin |
| 4,617,326 A | 10/1986 | Björnberg et al. |
| 4,624,868 A | 11/1986 | Muller |
| 4,693,713 A | 9/1987 | Chmelir et al. |
| 4,770,295 A | 9/1988 | Carveth et al. |
| 4,948,575 A | 8/1990 | Cole et al. |
| 5,089,606 A * | 2/1992 | Cole |

* cited by examiner

AQUEOUS GEL AND PACKAGE FOR A WOUND DRESSING AND METHOD

This is a continuation of application Ser. No. 07/774,064, filed Oct. 9, 1991, which was abandoned upon the filing hereof.

FIELD OF THE INVENTION

The invention relates to an aqueous gel for dressing wounds, as well as to a package for mixing solid and aqueous components and to a method of preparing the gel for application to a wound.

BACKGROUND OF THE INVENTION

The healing of wounds, such as wounds resulting from injury, surgical wounds or decubitus ulcers, is greatly dependent upon the dressing used. Conventional bandages often do not provide optimum results. In the case of a decubitus ulcer, treatment should include the removal of necrotic tissue and the establishment of an environment that enhances wound healing. Special pressure-relieving or reducing measures should also be taken. A moist dressing is often beneficial. Some of the advantages of a moist wound dressing are the rehydration of dehydrated tissue; increased angiogenesis, i.e., proliferation of new blood vessels; minimized bacterial growth; physical protection; and the maintenance of the proper pH for stimulating the release of oxygen and for allowing proteolytic enzymes to work more efficiently.

In the past, starches in granular form have been applied to wounds and dextrans have been applied as beads or as a paste. Calcium alginates have also been applied to wounds in powdered or granular form. These prior products have certain disadvantages. Powder or granules cannot be applied evenly. Consequently, they do not absorb tissue moisture evenly, causing nonhomogeneous hydration or swelling of the dry granules. Pastes must be spread onto the tissue. Generally speaking, granular absorbent dressings are difficult to remove completely from the wound bed. Dressing changes typically require irrigation of the wound bed to remove the gel granules. The pressure required to spread the paste can be painful or further traumatize the tissue. In addition, an even application is not always easy to achieve because the product retains its plastic character. If made part of a cloth bandage, the dressing may not have intimate contact with the tissue. In the case of a powder, sterility may be difficult to maintain because air containing airborne pathogens will enter the package, replacing and contaminating the powdered product as it is poured from the container.

British patent GB 2 229 443A describes a two component wound dressing that is a mixture of a gel-forming component together with a film forming component. This mixture forms a coherent film over the wound. The composition has to be kept refrigerated prior to use (pg. 3, lines 1–6). The gel former comprises block copolymers of polyoxyethylene-polyoxypropylene sold under the name Pluronic. The film formers comprise hydroxyethylcellulose, hydroxypropylmethylcellulose or polyvinyl alcohol. Unlike the present invention, these compositions have reversible thermosetting gel properties and have to be kept refrigerated prior to use (pg. 11, lines 14–15). The composition experiences a reversible temperature controlled liquid/gel transition at a temperature range of 16° C. to 20° C. By contrast, the present invention does not revert to a liquid upon heating or cooling and requires no film former, only a gel former. In tests conducted with the composition of the present invention through a range of 13° C. to 33° C., the gel was found to remain elastic but nonfluid, i.e., in a gelled condition and thus is a solid that is temperature non-reversible. This was shown by applying pressure to the surface of the gel with an instrument. As pressure is increased, the gel will deform and eventually fracture rather than flow around the instrument. Moreover, the hydrocolloid composition of the present invention is stored dry and is mixed with water just before use, preferably under sterile conditions, forming a dispersion which is initially fluid but which sets up without the necessity of a temperature change. The present invention does not contain a film former comprising a cellulose derivative or polyvinyl alcohol.

In view of these and other deficiencies of the prior art, it is a major objective of the invention to provide a sterile wound dressing and package enabling the dressing to be prepared from two components and which is initially fluid to facilitate application to the wound but which, after being applied, will form a stable, elastic gel in situ to protect the wound and maintain a moist environment at the tissue surface. Another object is to provide a dressing that is shelf stable yet is easily prepared and requires no refrigeration. Another object is to provide a gel for dressing wounds that holds its shape through a wide range of temperatures, i.e., that forms a solid that is temperature non-reversible, and can be removed from the wound bed in a solid plug. Still another object is to provide a dressing that will conform to the exact shape of the wound. The term "wound" herein include burn injuries. Yet another object is to provide a package that protects the dressing product, facilitates mixing and allows precise application to the wound. A further object is to provide a moist, initially fluid wound dressing which sets up in situ shortly after being applied, contains a quantity of moisture and, optionally, one or more medications or disinfectants to promote healing.

These and other more detailed and specific objects of the present invention will be apparent in view of the following description setting forth by way of example but a few of the various forms of the invention that will be apparent to those skilled in the art once the principles described herein are understood.

SUMMARY OF THE INVENTION

The invention provides a pourable, water-based natural or synthetic water soluble or water swellable gel forming hydrocolloidal polymeric gel for dressing wounds which is initially sufficiently fluid to be poured or spread into a wound but which after application forms a moist, solid elastic protective gel that contains a natural or synthetic polymeric hydrocolloid in a hydrated state. The liquid and solid components are initially separate. They are preferably contained in separate compartments of the same sealed container and are mixed just before use. The resulting aqueous hydrocolloid dispersion does not become solid immediately. The liquid component (water) gives the dispersion a fluid consistency initially. At this stage, the admixture is sufficiently fluid in consistency to allow it to be poured or spread into or onto the wound and to be precisely applied in the exact quantity and to the precise location required.

Following application, the dispersion of the hydrocolloid polymer composition will begin to solidify or coagulate to form a solid but elastic and pliable, self-supporting dressing structure consisting primarily of water and the hydrated natural or synthetic gel-forming polymeric hydrocolloid. A gelling agent such as a cross-linking composition can also be used advantageously with some of the hydrocolloids.

Water can be provided as one component of the package or, if desired, any available source of water can be used provided it is maintained in a sterile condition when mixed with the dry hydrocolloid. However, to best assure that the entire composition is sterile prior to application and the correct amount of water is used, it is preferred to provide the required water in either the same container as the solid ingredients or in a companion container which can be easily mixed with the solid constituents under sterile conditions. The resulting dressing sets up over the wound so as to become molded to the shape of the wound and contains a large quantity of moisture that will maintain the wound in a moist condition.

DETAILED DESCRIPTION OF THE INVENTION

In a preferred form of the invention, both solid and liquid constituents are prepackaged in separate compartments. The invention facilitates mixing of these constituents under sterile conditions while still enclosed the same package provided for shipping and storing the product. It is also preferred that a portion of the package be removed to enable the initially fluid gel, which is in a pourable condition, to be easily expelled onto the wound. The hydration of the hydrocolloid begins the moment the solid and liquid constituents come into contact with each other. The product, however, is liquid at this stage and therefore can be easily applied to cover or fill a wound of any shape. After application, the dressing occupies the void within a wound. The lower surface of the dressing has the same contour as the wound itself, i.e., the wound serves as a mold for shaping the dressing into a solid but flexible, three-dimensional form. The gel formed in the wound is also strong enough to allow for easy removal and to provide some cushioning for the wound bed, i.e., protecting the wound. Besides maintaining a moist wound surface, the dressing also absorbs exudate from the wound.

In a typical application, the freshly mixed solid and liquid components will remain fluid and pourable for about one to three minutes. The fresh mixture typically has a a viscosity of less than 6,000,000 cp at the beginning. At higher temperatures, the composition tends to solidify more rapidly. For example, at 34° C., a typical composition of the present invention reaches 6 million centipoise in about 25 minutes, whereas at 15° C. it takes an hour. Other factors that affect the length of time that the dispersion remains as a fluid and the ultimate strength of the gel include the chemical composition of the polymer and cross-linker, if any, as well as the concentration of each. It is highly preferred that the liquid dispersion have sufficient body or viscosity to allow the wound to be filled with little or no tendency to flow out of or away from the wound; i.e., it is preferred that the dressing is not watery enough to flow or drip from the wound.

The term "gel" herein refers to a solid or semi-solid, elastic, pliable substance formed by the solidification of an aqueous colloidal disperson. The term "fluid" refers to a water-based hydrocolloidal composition that has sufficient liquidity to be poured or spread onto a wound. The chemical composition of the natural or synthetic hydrocolloidal polymer employed should be selected to form a gel spontaneously after hydration or, if desired, the hydrocolloid can be one requiring a cross-linking agent to induce or enhance solidification of the polymer. The present invention encompasses both of these systems.

The unique wound dressing of the present invention is easy to ship and mix. It is also easy to apply and use. It is supple, elastic, pliable, soft, semi-solid and conforms naturally to the contours of the wound. The water in the dressing keeps the wound moist. The dressing is non-irritating, has no odor and promotes healing. The dressing will remain in place after application but can be easily removed when required.

Figures 1, 1A:
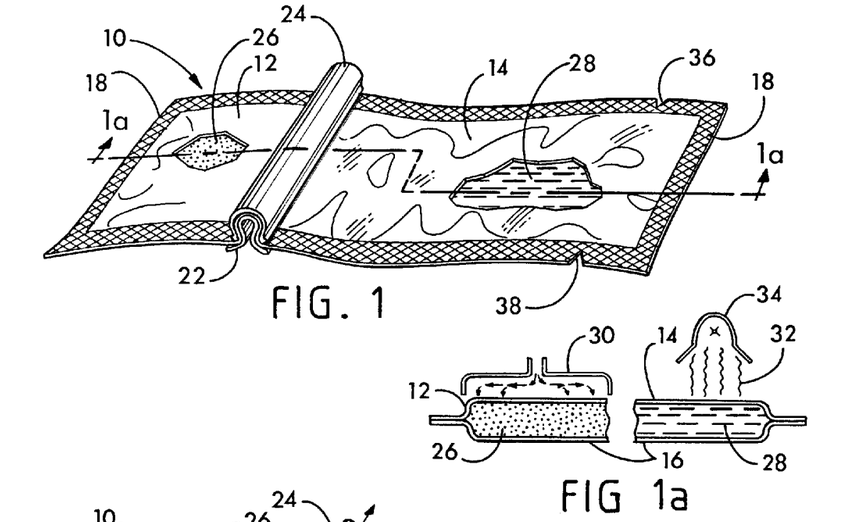
FIG. 1 is a perspective view illustrating one form of package used in accordance with the invention.
FIG. 1A is a semi-diagrammatic cross-sectional view taken on line 1A—1A of FIG. 1 showing sterilization of the package.

The invention is illustrated by way of example in FIGS. 1–8. Shown in FIGS. 1–8 is a receptacle or container 10, in this case a pouch formed from flexible sheet material including upper and lower sheets, in this case consisting of an upper sheet of paper 12, an upper sheet of plastic 14 and a lower sheet of plastic 16. The sheets are sealed together at their edges, e.g., by means of heat and pressure (a heat seal) to form a peripheral fin seal 18 which extends around the entire container 10. The paper sheet 12 is sealed to the plastic sheet 14 along a transverse seal line 20. Communication inside the container 10 on either side of the seal line 20 is prevented by means of a barrier, in this case a pair of inter-fitting inner and outer plastic C-shaped clips or channels 22 and 24, respectively, which are placed on opposite sides of the pouch 10 at the seal line 20 and snapped together with the pouch 10 pressed between them and forming a sharp bend in the pouch 10 over the inner clip 22. In this way, two separate compartments are formed, preventing contact between dry powder constituents 26 and liquid constituents 28 (water). The package 10 is shipped as shown in FIG. 1 with the water solution 28 separated from the dry gel-forming hydrocolloid 26 together with other desired ingredients such as dry cross-linking agents which at this stage are inactive.

Figure 2:
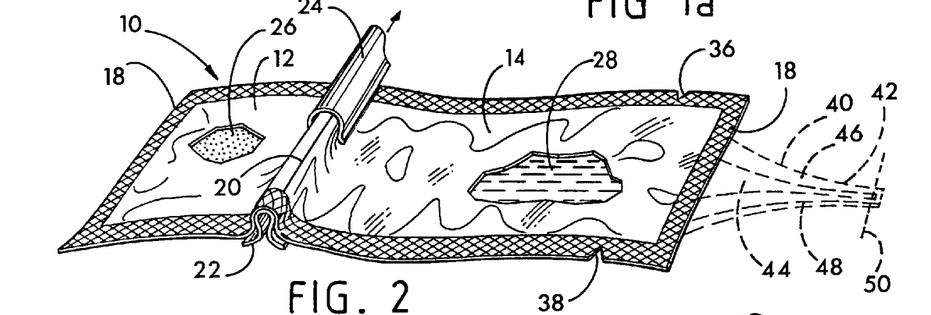
FIG. 2 is a view similar to FIG. 1 of an optional, a modified form of the package with a clip partially removed.

The package containing liquid and solid constituents 28, 26 is preferably sterilized. In this case, the contents are sterilized as shown in FIG. 1A. The paper sheet 12 is porous, allowing a sterilizing gas such as ethylene oxide to be introduced into the pouch 10 to the left of the barrier 22, 24, e.g. through a gas applicator manifold 30. The paper 12 is also impervious to pathogenic organisms. Exposure to ethylene oxide for a period of 360 minutes has been found satisfactory. To the right of the barrier 22, 24 the liquid constituents 28 are sterilized by being exposed to ionizing radiation 32 from a gamma radiation source 34 of $\geq 2.5$ Mrad. The paper sheet 12 can be 37.5-pound per ream porous, waterproof paper, e.g. Tyvek® paper (available from DuPont, Inc. of Wilmington, Del.), and the plastic sheets 14, 16 can be a 5 mil laminate, e.g. of polyethylene, aluminum foil and Mylar® as available from Technipaq Corporation of Chicago, Ill. Indentations 36, 38 can be provided at one end of the pouch to facilitate opening. In the alternative, as shown in FIG. 2, the pouch 10 can be provided with an extension 40 at one end which narrows to form a pointed dispensing point 42 containing a central duct 44 between edge seals 46 and 48. The dispensing point 42 can be cut with a scissors at 50 to provide a pointed spout through which the contents can be expelled when desired.

Figure 3:
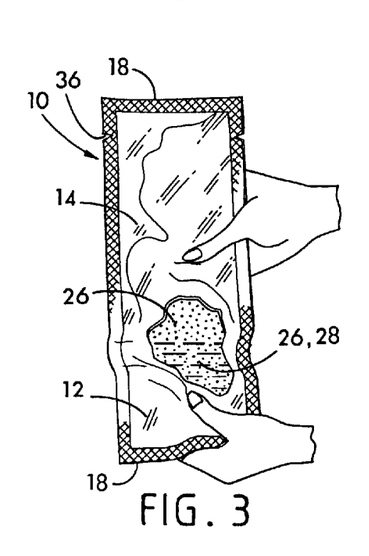
FIG. 3 is a view of the package of FIG. 1 on a smaller scale illustrating the mixing of its contents.

To use the package 10, the clips 22, 24 are removed by sliding portion 24 away from portion 22 as shown in FIG. 2. This allows communication between solid and liquid ingredients 26 and 28, respectively. Mixing of solid and liquid ingredients is accomplished manually as shown in FIG. 3, for about one minute until a homogeneous slurry is produced.

Figure 4:
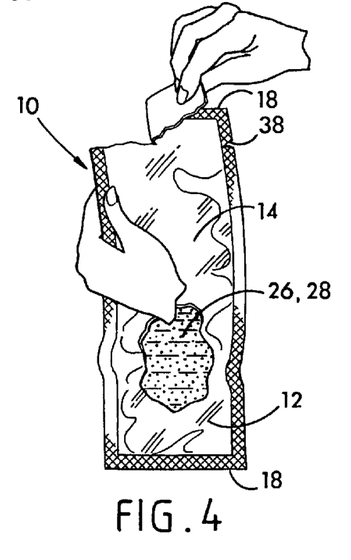
FIG. 4 is similar to FIG. 3 but shows the package being opened.
Figures 5, 6:
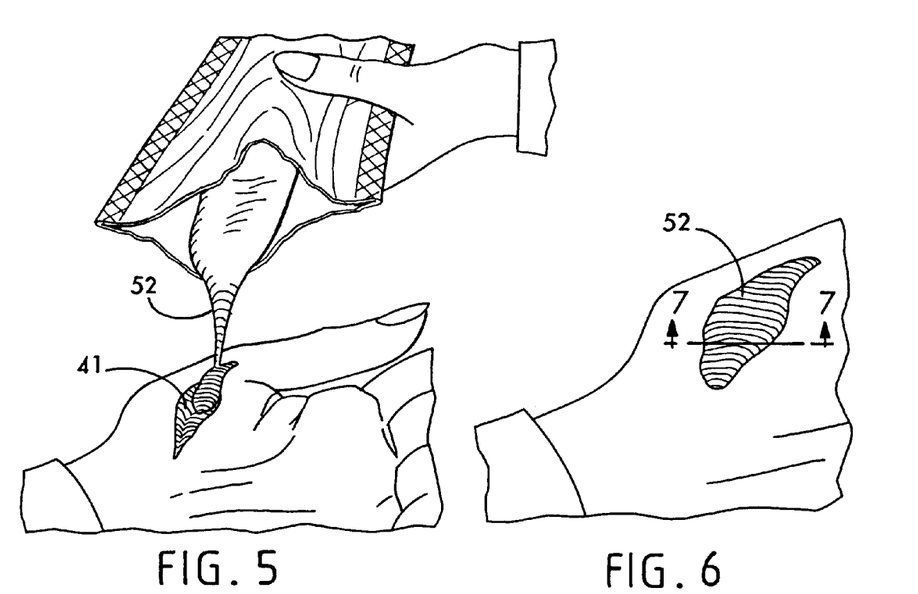
FIG. 5 illustrates the application of the dressing to a wound.
FIG. 6 illustrates the dressing after being applied to the wound.

As shown in FIG. 4, the end portion of the package 10 above the indentations 36, 36 is then removed. At this stage the aqueous hydrocolloid dispersion is a liquid and preferably sufficiently fluid to allow it to be poured into the wound as shown in FIG. 5. The dry solid constituents 26 begin to hydrate the moment the solid and liquid contact each other. After mixing, the mixture will remain fluid and pourable for typically about 1 to 3 minutes. During this time, while the hydrocolloid dispersion is fluid, it will typically have a viscosity of less than 6,000,000 cp (Brookfield). It should at least be sufficiently fluid to allow it to be easily spread onto the wound, e.g. with a spatula. However, pouring is preferred.

Figure 7:
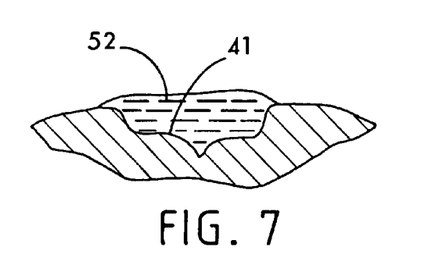
FIG. 7 is a vertical cross-sectional view taken on line 7—7 of FIG. 6 while the dressing is still fluid.
Figure 8:
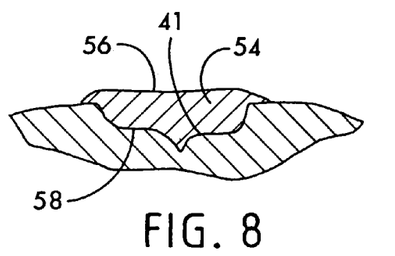
FIG. 8 is a view similar to FIG. 7 after the dressing has solidified to form a self-supporting gel.

It will be noticed that the liquid hydrocolloid mixture 52, as it is poured from the package 10 into the wound 41, will form a three-dimensional body substantially filling the wound; in other words, having a lower surface which conforms exactly to the shape of the wound. The hydrocolloid is in effect molded by the contour of the wound. Within a short time after application, typically five to ten minutes, the liquid hydrocolloid 52 solidifies to form a three-dimensional, self-supporting solid but elastic dressing body 54 with a substantially flat or slightly upwardly curved upper surface 56 and a lower surface 58 which conforms to the lower surface of the wound 41.

The combination of gas pervious and gas impervious materials in a single container has highly beneficial and unique properties, allowing a liquid to be held on one side of the barrier 22, 24 and a dry ingredient on the other side but both can be efficiently sterilized while in the same package. In this way, the package 10 provides for two kinds of sterilization in a single package. This is accomplished by providing two distinct components; paper 12 and plastic 14, 16. This eliminates the need for filling the package under sterile conditions which can substantially complicate and increase the cost of assembling packages. Thus, the invention provides the ability to mix two separate sterile components just before use. A sterile dressing can thus be delivered to a wound whenever needed with no requirement for refrigeration.

The invention can be applied to all kinds of wounds, including abrasions which are flat, but it is particularly useful in filling a wound which has a cavity or uneven surface. The unique wound dressing body 54 is easy to apply and use. The dressing 54 is supple, pliable, soft, solid but elastic, and conforms exactly to the contours of the wound 41. The moisture in the dressing 54 facilitates healing. The dressing is non-irritating, has little odor, and promotes healing. The dressing 54 will remain in place after being applied to the wound 41, but it can be easily removed later when required. Besides maintaining the wound 41 in a moist condition, the dressing 54 will absorb exudate from the wound as well as evaporate moisture from its top surface.

The solid dressing 54 is also non-cytotoxic. Removal of the dressing as a solid plug which is then weighed provides a convenient method of monitoring progress of wound healing. Since it is elastic, the dressing provides a cushioning function for the wound.

Figure 9:
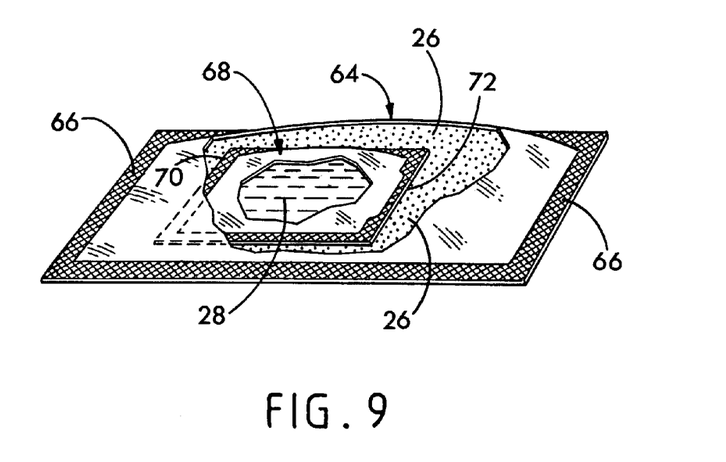
FIG. 9 shows a modified form of package.

Refer now to FIG. 9 which illustrates a package that includes a flexible envelope 64 similar to the envelop 12 sealed along its edges as shown at 66, e.g., by means of a heat seal, and containing the same dry powdered dressing composition 26 as well as a pressure-rupturable envelope 68 containing water in which is dissolved a cross-linking agent when used and sealed along its edges at 70 similar to the envelope 12 but having a rupturable section 72 in which the seal 70 is narrower and hence weaker to provide a sealed vent opening at 72 which will rupture when the envelopes 64 and 68 are pressed between the fingers, thereby expelling the water 28 from envelope 68 into the dry gel-forming hydrocolloid polymer particles 26. Continued manipulation causes the solid and liquid to mix, forming a sterile uniform dispersion which can be expelled onto the wound after the envelope 68 is opened.

The following method is used to form and use the package of FIG. 9. A predetermined quantity of water is sealed in pouch 68 and is then sterilized, e.g., by gamma radiation as described above. The pouch 68 and hydrocolloid particles 26 are then sealed in the envelope 64 which is preferably composed at least in part of a material such as Tyvek® which is permeable to a sterilizing gas. The envelope 64 is then exposed to a sterilizing gas, in this case ethylene oxide as described above. The package is then ready for use.

The hydrocolloid polymer particles employed can be any suitable biocompatible natural or synthetic gel forming hydrocolloid which, when mixed with water, will form a solid temperature non-reversible elastic gel, i.e., flexible hydrogel with or without a cross-linking agent to assist in the formation of a nonfluid dressing. Both the hydrocolloid and the cross-linking agent must, of course, be nontoxic. When boric acid is used as a cross-linking agent, it provides a bacteriostatic effect. Moisture evaporates from the dressing 54, thereby minimizing dimensional changes resulting from wound exudate absorption. Evaporation also cools the gel, which provides a soothing effect for the patient. While constituents can be sterilized before packaging, it is preferred to sterilize them after they are in the package as described above to more reliably ensure sterility.

If the gel forming hydrocolloid polymer is a natural polysaccharide gum, it is preferred that the molecular weight be typically between about 50,000 and 500,000. One preferred natural gum is guar gum in an amount between about 3% and 15% and preferably between 9% and 12%, the balance being water and trace quantities of cross-linker. Another suitable polymer is locust bean bum. Both guar and locust bean gum are polygalactomannan gums. While the quantities of the several components used in the get composition can be varied widely depending upon the properties employed, at least a sufficient amount of polymer should be provided to give the gel a solid consistency after being allowed to set in contact with the wound. Generally greater amounts of polymer and cross-linking agent provide a more solid dressing. Sufficient water should be present to provide the initial fluidity required for pouring or spreading the composition onto the wound. When a cross-linker is employed, only enough is needed to cause the polymer to solidify. For most applications, the cross-linking agent can be varied from about 0% to 8% by weight and preferably from about 0.1% to about 5.0% by weight, with the balance, e.g., about 80% to 95% by weight, being water. All quantities herein are expressed as percent by weight.

Any suitable nontoxic cross-linking agent of a composition can be used to form a chemical bond between the molecules of the polymer to gel the dispersion 52, forming a solid body. Examples of cross-linking agents for locust bean gum, guar or chemically modified guar are galactose, organic titanate, or boric acid.

When the hydrocolloid is a polyglucomanan (e.g., Konjak®), borax can be used as a cross-linking agent. When xanthan gum is used, a suitable cross-linker for xanthan gum is mannose. If locust bean gum is used as the principle hydrocolloid, lactose or other suitable oligosaccharide can be used. The cross-linked polymers lose water solubility as well as any ability to soften in response to temperature changes. Consequently, once solidified, the dressing is non-thermoplastic, i.e., it will not return to a liquid state by heating or cooling. When a cross-linking agent is used in the following examples, it is packaged with the water. However, if desired, it can be packaged with the dry ingredients.

If desired, any of the following substances can be included in the composition: medications and disinfectants as well as wound healing enhancers, e.g., vitamin preparations, blood coagulants for battlefield applications, antibiotic compounds, or a source of oxygen.

The invention will be better understood by reference to the following additional examples of some of the typical hydrocolloid compositions that can be employed in accordance with the invention in which quantities are expressed as percent by weight. All formulations are made at approximately room temperature (23° C.). Unless otherwise stated, the boric acid, borax or other cross-linking agent is dissolved in the water component.

| Ingredient | % by Weight | Comments |
|---|---|---|
| 1 | | |
| Hydroxy propyl guar* | 9.0 | Dressing thickened |
| Boric acid | 4.4 | very slowly, about |
| Borax | 0.6 | 5 minutes |
| Water | 86.0 | pH = 6.2 |
| 2 | | |
| Hydroxy propyl guar | 9.0 | Liquid phase |
| Boric acid | 4.5 | lasted less |
| Borax | 0.5 | than ten seconds. |
| Water | 86.0 | pH = 6.2 |
| 3 | | |
| Hydroxy propyl guar | 10.0 | Crosslinks slowly, |
| Boric acid | 4.2 | somewhat brittle |
| Borax | 0.8 | gel. |
| Water | 85.0 | pH = 6.5 |
| 4 | | |
| Guar (Supercol ®) | 10.0 | Short liquid |
| Water | 90.0 | phase, weak gel. |
| 5 | | |
| Boric acid | 3.6 | Very short liquid |
| Borax | 0.4 | phase, nice gel. |
| Guar (Supercol ®) | 5.0 | |
| Water | 87.0 | |
| 6 | | |
| Boric acid | 1.7 | Very short liquid |
| Borax | 0.3 | phase, chunky |
| Guar (Supercol ®) | 8.0 | gel. |
| water | 90.0 | |
| 7 | | |
| Cationic guar | 9.0 | Long liquid phase |
| Boric acid | 4.0 | and a soft gel. |
| Water | 87.0 | pH = 6.0 |
| 8 | | |
| Cationic guar | 10.0 | Hardened slightly |
| Boric acid | 5.0 | faster than |
| Water | 85.00 | example #7. |
| | | pH = 5.4 |
| 9 | | |
| Hydroxy propyl guar* | 11.0 | Very slow gel |
| Dihydroxy aluminum sodium carbonate (DHSC) | 1.0 | formation from liquid phase. |
| .9% saline (NaCl) | 88.0 | |
| 10 | | |
| Hydroxy propyl guar* | 10.0 | Nice gel within |
| Citric acid | .01 | 10 minutes. |
| .9% saline (NaCl) | 89.0 | pH = 6.7 |
| 11 | | |
| Hydroxy propyl guar* | 10.0 | Slightly weak |
| Boric acid | 1.0 | gel in 10 |
| Citric acid | .01 | minutes. |
| .9% saline (NaCl) | 89.0 | pH = 6.7 |
| 12 | | |
| Hydroxy propyl guar* | 10.0 | Nice gel in |
| Boric acid | 1.0 | 5 minutes. |
| Citric acid | 0.1 | pH = 5.8 |
| .9% saline (NaCl) | 89.0 | |
| 13 | | |
| Hydroxy propyl guar | 10.0 | Lumpy liquid |
| Boric acid | 0.5 | phase lasted |
| Citric acid | 0.05 | less than 15 |
| .9% saline (NaCL) | 89.5 | seconds. |
| | | pH = 6.6 |
| 14 | | |
| Hydroxy propyl guar | 10.0 | Nice gel in |
| Boric acid | 3.0 | 1 minute. |
| .9% saline (NaCL) | 87.0 | |
| 15 | | |
| Hydroxy propyl guar | 11.0 | Gel more |
| Boric acid | 1.0 | brittle than |
| .9% saline (NaCl) | 88.0 | elastic. |
| 16 | | |
| Hydroxy propyl guar | 10.0 | Liquid phase |
| Boric acid | 1.0 | less than 2 |
| .9% saline (NaCL) | 89.0 | minutes; great gel in 30 minutes. pH = 6.6 |
| 17 | | |
| Hydroxy propyl guar | 10.0 | Pourable liquid |
| Boric acid | 0.5 | after exactly 1 |
| .9% saline (NaCL) | 89.5 | minute, weak gel. pH = 7.0 |
| 18 | | |
| Hydroxy propyl guar | 5.0 | Liquid for 30 |

-continued

| Ingredient | % by Weight | Comments |
|---|---|---|
| Boric acid | 1.0 | seconds, good gel. |
| Guar (Supercol ®) | 5.0 | pH = 6.1 |
| .9% saline (NaCl) | 89.0 | |
| 19 | | |
| Hydroxy propyl guar | 5.0 | Gel formed more slowly than example #18. |
| Boric acid | 0.5 | |
| Guar (Supercol ®) | 5.0 | |
| .9% saline (NaCl) | 89.5 | pH = 6.6 |
| 20 | | |
| Cationic guar* | 5.0 | Two-phase liquid, chunky gel produced rapidly. |
| Boric acid | 1.0 | |
| Guar (Supercol ®) | 5.0 | |
| .9% saline (NaCl) | 89.0 | pH = 6.9 |
| 21 | | |
| Hydroxy propyl guar | 9.0 | Pourable in 1 minute, strong gel. |
| Boric acid | 0.25 | |
| Galactose | 2.0 | |
| .9% saline (NaCl) | 88.75 | pH = 6.5 |
| 22 | | |
| Hydroxy propyl guar | 9.0 | Mixable liquid 1 minute, strong gel. |
| Boric acid | 0.5 | |
| Galactose* | 2.0 | |
| .9% saline (NaCl) | 88.5 | pH = 6.4 |
| 23 | | |
| Hydroxy propyl guar | 9.0 | Gel formed in less than 2 minutes, strong gel in 5 minutes. |
| Boric acid | 0.25 | |
| Galactose | 3.0 | |
| .9% saline (NaCl) | 87.75 | |
| | | pH = 6.7 |
| 24 | | |
| Cationic guar | 9.0 | Homogeneous liquid more than 3 minutes. |
| Boric acid | 1.0 | |
| Galactose | 1.0 | |
| Mannose | 2.0 | pH = 6.3 |
| .9% saline (NaCl) | 87.0 | |
| 25 | | |
| Cationic guar | 9.0 | Pourable liquid in 2 minutes. |
| Boric acid | 1.0 | |
| Galactose | 3.0 | pH = 6.2 |
| .9% saline (NaCl) | 87.0 | |
| 26 | | |
| Cationic guar | 9.0 | Thickened more slowly than example #25. |
| Boric acid | 1.0 | |
| Mannose | 3.0 | |
| .9% saline (NaCl) | 87.0 | pH = 6.3 |
| 27 | | |
| Hydroxy propyl guar | 9.0 | Gel slightly weaker, more elastic. |
| Boric acid | 0.5 | |
| Lactose | 3.0 | |
| Water | 87.5 | pH = 7.1 |
| 28 | | |
| Hydroxy propyl guar | 9.0 | Clear translucent gel, fair strength and resilience. |
| Calcium chloride | 3.0 | |
| Citric acid | 0.5 | |
| Water | 87.5 | pH = 2.8 |
| 29 | | |
| Hydroxy propyl guar | 9.0 | White, very tough elastic gel. |
| Magnesium carbonate | 2.0 | |
| Citric acid | 0.25 | |
| Water | 88.75 | pH = 7.6 |
| 30 | | |
| Hydroxy propyl guar | 9.0 | Nice gel, fairly weak. |
| Potassium antimony tartrate | 2.0 | pH = 6.4 |

-continued

| Ingredient | % by Weight | Comments |
|---|---|---|
| Water | 89.0 | |
| 31 | | |
| Hydroxy propyl guar | 9.0 | Translucent gel pH = 7.4 |
| Tyxor* | 2.0 | |
| Water | 89.0 | |
| 32 | | |
| Anionic guar | 12.0 | Much stronger gel than example #31. |
| Boric acid | 0.63 | |
| Borax | 4.37 | |
| Water | 83.0 | pH = 6.1 |
| 33 | | |
| Glucomanan (Konjak ®) | 12.0 | Long liquid phase, weak gel. |
| Boric acid | 2.0 | |
| Water | 86.0 | pH = 5.4 |
| 34 | | |
| Hydroxy propyl guar | 12.0 | Low cross-linking, slimy gel. |
| Borax | 0.5 | |
| Alum | 3.0 | |
| Water | 84.5 | pH = 4.1 |
| 35 | | |
| Hydroxy propyl guar | 12.0 | Gel had low cohesive strength. |
| Calcium phosphate | 3.0 | |
| Citric acid | 0.1 | |
| Water | 84.9 | pH = 6.8 |
| 36 | | |
| Hydroxy propyl guar | 12.0 | Gel had low cohesive strength. |
| Calcium sulfate | 3.0 | |
| Citric acid | 0.1 | |
| Water | 84.9 | pH = 5.9 |
| 37 | | |
| Xanthan gum | 10.0 | Rapid surface hydration. |
| Boric acid | 3.0 | |
| Water | 87.0 | |
| 38 | | |
| Xanthan gum | 3.0 | Lumps from rapid surface |
| Hydroxy propyl guar | 6.0 | |
| Boric acid | 0.25 | |
| Galactose | 2.0 | |
| Water | 88.75 | |
| 39 | | |
| Xanthan gum | 5.0 | Lumps from rapid surface hydration. |
| Locust bean gum | 5.0 | |
| Boric acid | 3.0 | |
| Water | 87.0 | |
| 40 | | |
| Potassium alginate | 3.1 | Stiff, gritty gel. |
| Calcium sulfate | 3.1 | |
| Trisodium phosphate | 1.6 | |
| Diatomaceous earth | 12.2 | |
| Water | 80.0 | |
| 41 | | |
| Sodium alginate | 3.55 | Stiff gel, not very elastic. |
| Calcium sulfate | 3.55 | |
| Sodium pyrophosphate | 0.71 | |
| Fine diatomaceous earth | 21.28 | |
| Water | 70.91 | |
| 42 | | |
| Boric acid | 3.0 | Gel strength moderate to low |
| Borax | 5.0 | |
| Guar (Supercol ®) | 3.0 | |
| Water | 89.0 | |

-continued

| Ingredient | % by Weight | Comments |
|---|---|---|
| 43 | | |
| Hydroxy propyl guar | 15.0 | Gel like |
| Calcium sulfate | 3.5 | example #36 |
| Citric acid | 0.1 | except somewhat |
| Water | 81.4 | greater cohesive strength. |

*Galactasol 418 ®, a hydroxy propyl guar manufactured by the Aqualon Company of Wilmington, Delaware. The hydroxy propyl group can be linked to either the galactose or mannose base of the guar molecule.
*Galactasol 418 ®, Aqualon Company of Wilmington, Delaware.
*Enhance ®, Aqualon Company of Wilmington, Delaware.
*Other samples are made in which galactose is replaced by galactose pentasaccharide or mannose tetrasaccharide. Another sample is made with a tetrasaccharide containing both mannose and galactose in equal quantities.
*An organic titanate, namely, titanium-ammonium lactate chelate, available from E.I. duPont of Wilmington, Delaware.

Many variations of the present invention within the scope of the appended claims will be apparent to those skilled in the art once the principles described herein are understood.

What is claimed is:

1. A hydrated wound dressing comprising,
    about 70–95% by weight water,
    about 3–15% by weight of a natural or synthetic hydrophilic hydrocolloid gel-forming polymer,
    the amount of hydrocolloid relative to the amount of said water being effective to form a fluid hydrocolloid dispersion in the water having an initial viscosity of less than about 6,000,000 cPs at 34° C. after said hydrocolloid is mixed with said water,
    said dressing being applied to the wound as said fluid hydrocolloid dispersion and thereafter becoming an elastic body adapted to maintain the wound in a moist condition, to conform to the contours of the wound, to absorb exudate from the wound, and to cushion the wound,
    said dressing being solidified in situ upon the wound as a solid body having a molded surface corresponding to the shape of the wound, and
    said solid body being removable from the wound as a solid plug to facilitate cleaning the wound, monitoring the progress of wound healing, and changing the dressing.

2. The dressing of claim 1 in combination with a crosslinking agent to aid in solidifying the polymer.

3. The dressing according to claim 1 wherein the gel-forming polymer is a member selected from the group consisting of guar gum, hydroxypropyl guar, cationic guar, anionic guar, glucomannan, galactomannan, xanthan gum, locust bean, algin and the cogeners thereof.

4. The dressing according to claim 2 wherein the crosslinking agent is a member selected from the group consisting of borax, boric acid, a source of borate ions, an organic titanate, galactose, mannose, lactose, an oligosaccharide containing a monomer selected from galactose or mannose, a source of water soluble cations of calcium, magnesium or aluminum and the cogeners thereof.

5. The dressing according to claim 2 wherein the polymer is present in the amount of from about 3% to 15% by weight and the crosslinking agent is present in the amount of from about 0.1% to about 5.0% by weight.

6. The dressing according to claim 2 wherein the polymer comprises guar gum or a biologically compatible salt thereof in the amount of from about 8% to 15% by weight and the crosslinking agent comprises boric acid in the amount of from about 0.1% to about 1.0% by weight.

7. A wound dressing contained in an applicator package for storing, mixing and applying said dressing to a wound to provide a solid elastic wound dressing, said wound dressing comprising:
    a hydrocolloid polymer in particulate form comprising a member selected from the group consisting of guar gum, glucomannan, galactomannan, hydroxypropyl guar gum, cationic guar gum, anionic guar gum, xanthan gum, locust bean gum, algin and the cogeners thereof contained within a first compartment in said package;
    water contained within a second compartment in said package;
    said hydrocolloid polymer in said first compartment and said water in said second compartment being separated from each other by means of a removable barrier to provide communication between said first and second compartments when the barrier is removed so that the water and hydrocolloid polymer can be mixed within the package while maintaining the sterility thereof;
    the amount of said hydrocolloid polymer relative to the amount of water being effective to produce a) a fluid hydrocolloid dispersion after said hydrocolloid is mixed with said water in said package whereby said mixing forms a fluid dispersion that can be applied to a wound from the package and b) is thereafter capable of setting up to form a solid moist aqueous gel dressing in situ while in contact with the wound and the dressing is an elastic body molded to the shape of the wound after solidifying thereon.

8. The wound dressing of claim 7 wherein the dressing includes a crosslinking agent to aid in the solidification of the hydrocolloid polymer.

9. A method for preparing, applying and forming a solid wound dressing which comprises:
    placing a water-soluble or water-swellable hydrocolloid polymer comprising a member selected from the group consisting of guar gum, glucomannan, galactomannan, hydroxypropyl guar gum, cationic guar gum, anionic guar gum, xanthan gum, locust bean gum, algin and the cogeners thereof in particulate form into a first compartment of a package;
    placing water in a second compartment of said package;
    sealing said first and second compartments with a manually-removable barrier so that the contents of each compartment cannot intermix while said barrier is in place;
    removing said barrier and hydrating the hydrocolloid polymer by mixing said water with said polymer within said package to form a fluid hydrocolloid polymer dispersion,
    adjusting the amount of said hydrcolloid relative to the amount of said water to be
        a) effective to produce a fluid hydrocolloid dispersion which can be poured or spread onto a surface after said hydrocolloid is mixed with said water and
        b) capable of setting up to form a solid aqueous dressing molded to the shape of the wound,
    applying the fluid dispersion onto the wound and/or skin surface while the dispersion is in a fluid state so as to conform to the surface of the wound; and
    allowing the dispersion to solidify on the wound to form an elastic dressing body in situ over the wound.

10. The method of claim 9 wherein said package includes a crosslinking agent for crosslinking the hydrocolloid, said crosslinking agent comprising a member selected from the group consisting of boric acid, borax, an organic titanate, galactose, mannose, lactose, an oligosaccharide containing a monomer selected from galactose or mannose, and a source of water soluble cations selected from calcium, magnesium or aluminum.

11. The dressing of claim 4 including a crosslinking agent which comprises a member selected from the group consisting of boric acid, borax, an organic titanate, galactose, mannose, lactose, an oligosaccharide containing galactose or mannose, and a source of soluble cations selected from calcium, magnesium or aluminum.

12. The method of claim 9 wherein the first compartment of the package is made from a gas porous sheet and the hydrocolloid polymer is sterilized within the compartment by introducing a sterilizing gas into the package through the porous sheet.

13. The method of claim 9 wherein the water is sterilized by exposing said water to ionizing radiation.

14. The wound dressing of claim 7 which further includes a medicament in said water or said hydrocolloid polymer.

15. The wound dressing of claim 7 wherein the medicament is selected from the group consisting of a disinfectant, a wound-healing enhancer, a vitamin, a blood coagulant, an antibiotic.

\* \* \* \* \*